United States Patent [19]

Morris

[11] Patent Number: 4,553,539

[45] Date of Patent: Nov. 19, 1985

[54] BILATERAL FENESTRATED DRAPE

[75] Inventor: Henrietta K. Morris, Arlington, Tex.

[73] Assignee: Surgikos, Inc., Arlington, Tex.

[21] Appl. No.: 538,060

[22] Filed: Sep. 30, 1983

[51] Int. Cl.⁴ .............................................. A61F 13/00
[52] U.S. Cl. ................................................. 128/132 D
[58] Field of Search ..................................... 128/132 D

[56] References Cited

U.S. PATENT DOCUMENTS

| | | | |
|---|---|---|---|
| 3,335,719 | 8/1967 | Boucher | 128/132 D |
| 3,537,446 | 11/1970 | Rowland | 128/132 D |
| 3,542,019 | 11/1970 | Gittins | 128/132 D |
| 4,354,486 | 10/1982 | Oliver | 128/132 D |

Primary Examiner—Stephen C. Pellegrino
Assistant Examiner—Sherri E. Vinyard
Attorney, Agent, or Firm—Michael Q. Tatlow

[57] ABSTRACT

A bilateral fenestrated drape folded in such a manner to eliminate the need for removable paper coverings over the fenestrations. The drape is fan folded in the longitudinal direction and then fan folded transversely to form two stacks of the folds with a bridging or central portion between the stacks. The bridging portion is folded to form flaps which are used to cover the fenestrations.

3 Claims, 10 Drawing Figures

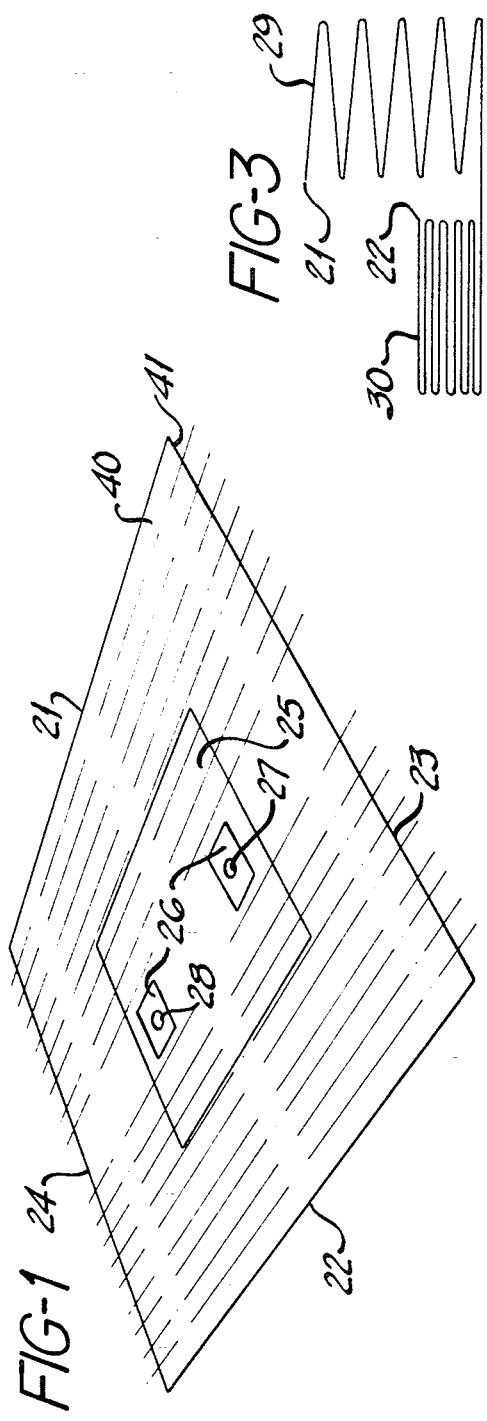
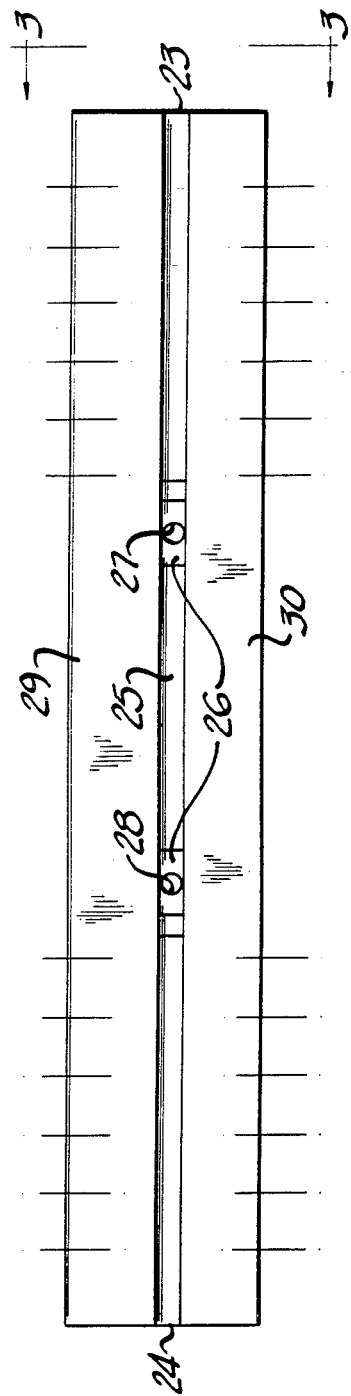

BILATERAL FENESTRATED DRAPE

The present invention relates to fenestrated drapes and, more particularly, to bilateral fenestrated drapes and to a novel fold for a bilateral fenestrated drape.

BACKGROUND

Disposable surgical drapes are commonly used in the operating room to protect the patient from possible bacterial contamination from the environment of the operating room and the surgical staff. With the widespread use of disposable surgical drapes, drapes have been designed for particular surgical procedures, thereby, allowing better draping techniques and ease in maintaining proper sterile procedures in the operating room. A large number of such drapes contain precut openings or fenestrations in the drape, which are placed over the site of the surgical procedures. The use of preformed or precut fenestrations allows improved draping techniques.

With the use of fenestrated drapes, it is often necessary to cover the fenestration in the packaged drape with a removable, protective cover to prevent possible contamination of the drape during the placement of the drape on the patient. The proper aseptic technique in the operating room would indicate that if the upper surface of the drape is contacted while the drape is being placed on the patient, the drape would be considered to be contaminated. In order to prevent this, a protective paper covering is placed on the upper surface of the drape over the fenestration. The use of the paper covering prevents the inadvertent contact of the upper surface of the drape during the draping procedure. The drape is placed on the patient, and, after the drape is in position, the covering is removed.

The present invention, more particularly, relates to a bilateral fenestrated drape in which there are two fenestrations spaced apart along a central axis of the drape. Drapes of this type are used in surgery on the extremities. There are two fenestrations in the drape, and there is an insert of an elastic material securely fitted in each fenestration. The elastic material also has a fenestration which is usually a circular opening but may be other shapes. When the partially opened drape is placed on the patient, the extremities are passed through the fenestrations in the elastic material to isolate that portion of the limb or limbs that will be the operative site of the surgery from the remainder of the patient's body. The elastomeric insert in the fenestration is capable of stretching to tightly conform to the limb. Drapes of this type usually require two removable inserts over the fenestrations to protect the upper surface of the drape from possible contamination through the fenestrations.

SUMMARY OF THE INVENTION

It is the object of the present invention to provide a bilateral fenestrated drape which can be assembled and folded in such a fashion as to avoid the need for the protective coverings over the fenestration.

The bilateral fenestrated drape of the present invention is folded with the fenestrations on the lower surface of the drape. The drape material between the fenestrations is then folded over the lower surface of the fenestrations to protect the upper surface of the drape from inadvertent contact through the fenestrations.

BRIEF DESCRIPTION OF THE DRAWINGS

FIG. 1 is a plan view of the drape in an open position and prior to any folding of the drape.

FIG. 2 shows the drape after being folded along transversely extending fold lines.

FIG. 3 is an end view of the drape taken in the direction of lines 3—3 of FIG. 2.

DETAILED DESCRIPTION OF THE INVENTION

Figure 4:
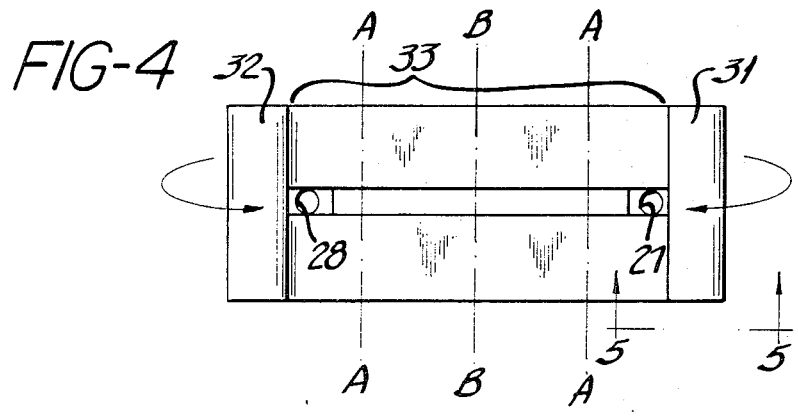
FIG. 4 shows the drape partially folded from the transverse ends toward the center of the drape.

Referring to the drawings where like reference characters are utilized to identify like parts throughout the several views, there is shown in FIG. 1 an isometric plan of the drape of the present invention. The drape has a top edge 21 which extends toward the head of the patient when the drape is in use. The drape has a bottom edge 22 opposite the top edge and lateral or side edges 23 and 24. The drape has a lower surface 41 in contact with the patient's body when the drape is in use and an upper surface 40 opposite the lower surface. There is a reinforcement area 25 on the upper surface of the drape. The reinforcement may be an impervious plastic film with an absorbent material covering the film. The film side of the reinforcement is secured to the upper surface of the main sheet of the drape. The absorbent material is on the upper surface of the finished drape. The purpose of the reinforcement is to provide an impervious area to prevent liquid from penetrating the drape around the fenestrations and to provide an absorbent surface around the area of the fenestrations. The main body of the drape is made with a nonwoven fabric which has a repellent finish. There are two openings which extend through the reinforcement and through the main sheet of the drape. Inserted in these openings is a thin sheet of a stretchable elastic material. This elastic material is made from natural or synthetic rubber. A preferred material is an A-B-A type block copolymer in which A represents polystyrene end blocks, and B represents a poyolefin rubber midblock. Such material is available from Shell Chemical Company under the name KRATON TM thermo-plastic rubber. There are fenestrations 27 and 28 through this elastic insert. This fenestration will stretch as the limb is fit through the fenestration to form a tight seal around the patient's limb.

The main sheet of the drape is approximately 116 inches×80 inches. The main sheet is folded around a number of transversely extending fold lines, as shown in FIG. 1. The longitudinal dimension of the drape is folded along these lines to form two stacks of fan folds 29 and 30 which overlie the upper surface of the central portion of the main sheet of the drape, but exposing both fenestrations as shown in FIG. 2. The fan folds are approximately 5⅜ inches in width, and the folded drape is from 11 to 13 inches wide. In the drape construction shown in FIG. 1, a line passing through the fenestrations is on the center line of the drape, and the edges of fan folded stacks 29 and 30 are spaced ½ inch to 1½ inches from the edges of the fenestration as shown in FIG. 2. It should be understood that the drape can be constructed so that a line passing through the fenestrations is not on the central line of the drape but may be along a line which is in the upper or lower ⅓ of the drape. In that case, the fan folded segments would not have an equal number of folds, but the drape would be folded so that each stack of longitudinal folds are adjacent but do not overlie the fenestrations of the drape.

If the fan folded segments or a portion thereof overlie the fenestrations, there would be some possiblity that the upper surface of the drape could be contaminated when the drape was applied to the patient.

Figure 5:
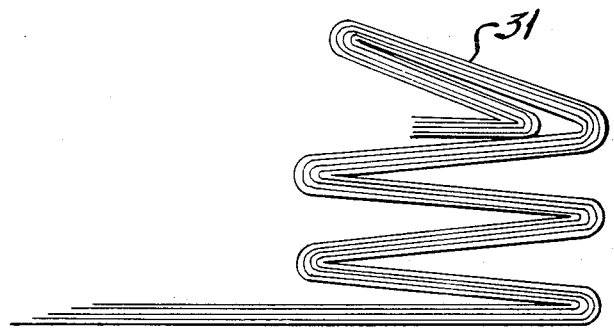
FIG. 5 is an end view of the drape taken along the lines 5—5 in FIG. 4.

The longitudinal folding of the drape shown in FIGS. 1-3 reduces the size of the drape in the longitudinal direction. The transverse or lateral edges 23 and 24 of the drape are then fan folded towards the fenestrations, as shown in FIGS. 4 and 5. The drape thus folded is composed of two fan folded stacks 31 and 32 of the drape and a central or bridging portion 33 of the drape, which is not yet folded. There is a fenestration on the lower surface of each of the stacks of folds. This central portion 33 of the drape will be folded in a configuration to enable a portion of the drape material from the central portion to be folded into a flap which will overlie the fenestrations on the lower surface of the folded drape to eliminate the need for separate paper covers to cover the fenestration prior to the application of the drape to the patient.

Figure 6:
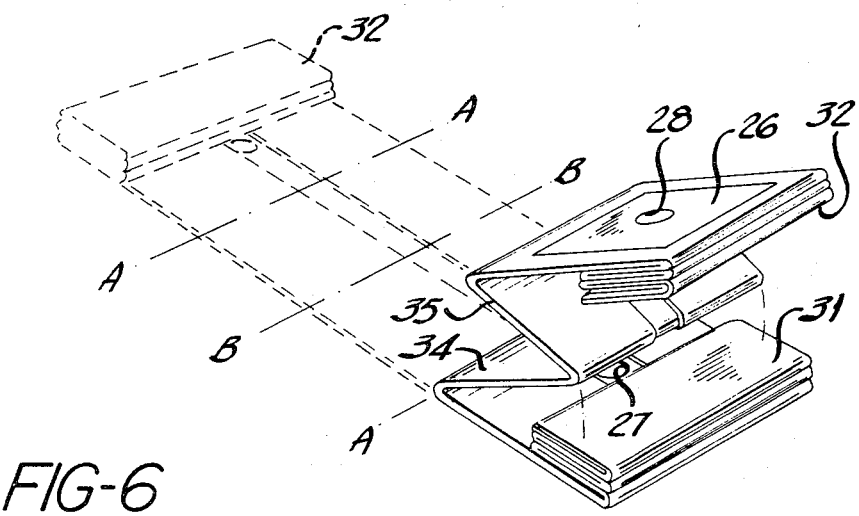
FIG. 6 shows the folding sequence of the drape to laterally fold the drape into a single stack.
Figure 7:
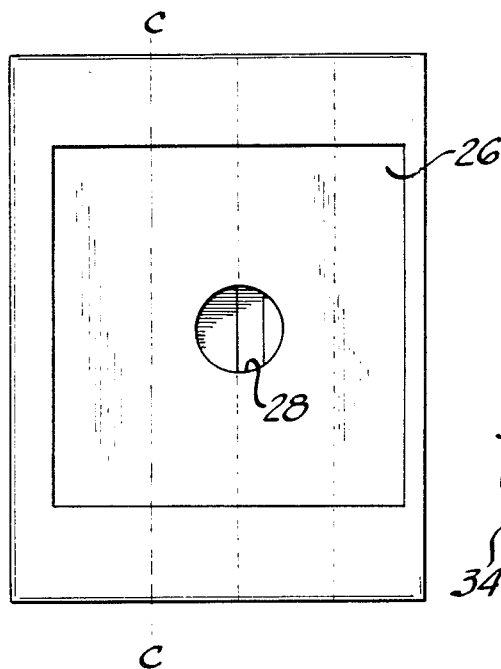
FIG. 7 is a top view of the drape showing the subsequent fold lines for the completion of the fold sequence.
Figure 8:
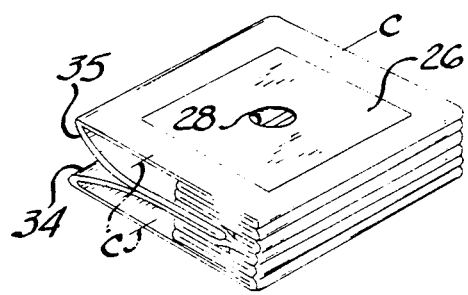
FIG. 8 is an isometric view of the drape folded as shown in FIG. 7.
Figure 9:
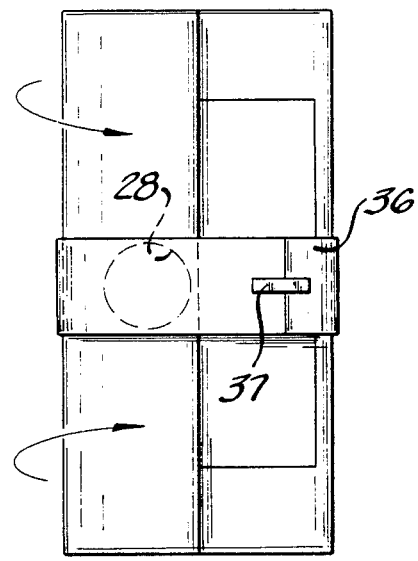
FIG. 9 is a top view of the completely folded drape.
Figure 10:
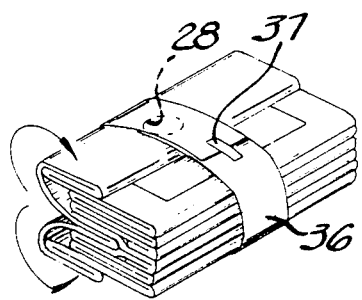
FIG. 10 is an isometric view of the completely folded drape.

The drape, as shown in FIG. 4, is folded along the lines A—A toward a center line B to provide two flaps 34 and 35, shown in FIG. 6, which are used to cover the fenestrations in the drape. The folding sequence, as shown in FIG. 6, provides the drape configuration which is shown in FIGS. 7 and 8. Each flap 34 or 35 is then folded along a fold line C—C, shown in FIGS. 7 and 8, so that the portion of the flap overlies the fenestration on each side of the drape, as shown in FIGS. 9 and 10. The drape may then be secured in this configuration by a paper band 36 secured in position by a piece of adhesive tape 37.

The drape is finally folded into a relatively compact package, as shown in FIG. 10. When the drape is to be applied to a patient, the paper band 36 can be removed and the drape opened into the configuration shown in FIG. 4. The patient's limbs would then be fitted through the fenestrations, and the drape would then be opened along its transverse dimension and then along its longitudinal dimension to cover the patient.

I claim:

1. A bilateral, fenestrated, surgical drape comprising a rectangular main sheet having an upper surface and a lower surface, a top edge, a bottom edge and two opposing side edges, two fenestrations spaced apart from each other and spaced inwardly from the side edges of the drape and located along a line parallel to said top and bottom edges, a portion of the main sheet between said line and the top edge and a portion of the main sheet between said line and the bottom edge being fan folded in the longitudinal direction to form two longitudinally folded stacks of folds, the longitudinally folded stacks of folds overlying the upper surface of the drape, and the inner edge of the longitudinally folded stacks lying adjacent the fenestrations, the longitudinally folded stacks being fan folded from the side edges of the drape to form two transversely folded stacks of folds overlying a portion of the upper surface of the main sheet adjacent each of the fenestrations and separated by a central portion of the drape between the transversely folded stacks, the central portion of the drape being folded along fold lines toward a fold line passing through the center of said central portion to form two flaps, the flaps being folded over the lower surface of the drape to cover the fenestrations.

2. The drape of claim 1 on which there is a reinforcement area surrounding the fenestrations, and the fenestrations are formed in elastic inserts in the reinforcement area of the drape.

3. The drape of claim 2 in which the flaps are secured over the fenestration with a removable band.

* * * * *